(12) United States Patent
Chen et al.

(10) Patent No.: US 10,300,094 B2
(45) Date of Patent: May 28, 2019

(54) METHOD AND COMPOSITION FOR INHIBITING BACTERIAL ADHESION OF ORAL PATHOGENS

(71) Applicant: GENMONT BIOTECH INC., Tainan (TW)

(72) Inventors: Yi-Hsing Chen, Tainan (TW); Ya-Hui Chen, Chiayi County (TW); Chien-Chen Wu, Taipei (TW)

(73) Assignee: GENMONT BIOTECH INC., Tainan (TW)

( * ) Notice: Subject to any disclaimer, the term of this patent is extended or adjusted under 35 U.S.C. 154(b) by 283 days.

(21) Appl. No.: 15/176,773

(22) Filed: Jun. 8, 2016

(65) Prior Publication Data

US 2017/0281698 A1    Oct. 5, 2017

(30) Foreign Application Priority Data

Apr. 1, 2016    (TW) .............................. 105110614 A (51) Int. Cl.
| | | |
|---|---|---|
| *A61K 35/747* | (2015.01) | |
| *A61K 9/00* | (2006.01) | |
| *A61Q 11/00* | (2006.01) | |
| *A61K 8/99* | (2017.01) | |

(52) U.S. Cl.
CPC .............. *A61K 35/747* (2013.01); *A61K 8/99* (2013.01); *A61K 9/0053* (2013.01); *A61K 9/0063* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 2008/0118444 A1 | 5/2008 | Hsu et al. | |
| 2012/0230923 A1 | 9/2012 | Cooper | |
| 2013/0344010 A1* | 12/2013 | Pompejus | ................ A61K 8/99 |
| | | | 424/50 |
| 2014/0065218 A1* | 3/2014 | Lang | .................... A61K 35/744 |
| | | | 424/474 |

FOREIGN PATENT DOCUMENTS

| | | |
|---|---|---|
| EP | 2449891 A1 | 5/2012 |
| EP | 2455095 A1 | 5/2012 |
| WO | WO2012062868 A1 | 5/2012 |
| WO | WO2012100991 A1 | 8/2012 |
| WO | WO2015000082 A1 | 1/2015 |

OTHER PUBLICATIONS

Holz et al., Lactobacillus paracasei DSMZ16671 Reduces Mutans Streptococci: A Short-Term Pilot Study, Probiotics & Antimirco Prot., Sep. 8, 2013, pp. 259-263, 5.

\* cited by examiner

*Primary Examiner* — Vera Afremova
(74) *Attorney, Agent, or Firm* — Wpat, PC (57) ABSTRACT

A method for inhibiting bacterial adhesion of oral pathogens, comprising administering a heat-inactivated *Lactobacillus* strain to a subject in need to inhibit bacterial adhesion of oral pathogens is disclosed. The *Lactobacillus* strain is selected from *Lactobacillus paracasei* GMNL-143, *Lactobacillus helveticus* GMNL-164 or *Lactobacillus rhamnosus* GMNL-464. A composition for inhibiting bacterial adhesion of oral pathogens is also disclosed.

2 Claims, 6 Drawing Sheets

Specification includes a Sequence Listing.

METHOD AND COMPOSITION FOR INHIBITING BACTERIAL ADHESION OF ORAL PATHOGENS

CROSS REFERENCE TO RELATED APPLICATIONS

This application claims the benefit of Taiwan application serial No. 105110614, filed on Apr. 1, 2016, and the subject matter of which is incorporated herein by reference.

BACKGROUND OF THE INVENTION

Field of the Invention

The present invention generally relates to a method for inhibiting bacterial adhesion of oral pathogens and, more particularly, to a method for inhibiting bacterial adhesion of oral pathogens by administering a heat-inactivated *Lactobacillus* strain. The present invention further relates to a composition for inhibiting bacterial adhesion of oral pathogens.

Description of the Related Art

The mouth harbors a diverse, abundant and complex microbiota, which probably accumulates on both the hard and soft oral tissues in biofilms. The microbiota may not only vary according to change in oral environment such as the appearance of the teeth, but also be different because of the dietary and living habits.

Oral microbiota plays an important role in the dental diseases. For example, *Streptococcus mutans* produces acidic substances following fermentation of dietary sugars, destroying the tooth surface (enamel) and resulting in dental caries. Biofilms surrounding the gingival crevice area formed by anaerobic bacterium such as *Porphyromonas gingivalis* or *Prevotella intermedia* may result in inflammation and periodontal disease. Moreover, the volatile sulfur compounds (VSCs) produced by breakdown of sulfur containing amino acids by *P. gingivalis*, *P. intermedia* or *Fusobacterium nucleatum* are the major reason of halitosis. Therefore, regulating the distribution of oral microbiota by probiotics can prevent from dental diseases, such as dental caries, periodontal disease and halitosis.

In light of this, it is necessary to provide a method and a composition for inhibiting bacterial adhesion of oral pathogens.

SUMMARY OF THE INVENTION

It is therefore the objective of this invention to provide a method with a heat-inactivated *Lactobacillus* strain to inhibit bacterial adhesion of oral pathogens.

It is another objective of this invention to provide a composition including a heat-inactivated *Lactobacillus* strain to inhibit bacterial adhesion of oral pathogens.

A first embodiment of the invention discloses a method for inhibiting bacterial adhesion of oral pathogens. The method comprises administering a heat-inactivated *Lactobacillus* strain to a subject in need to inhibit bacterial adhesion of oral pathogens. The *Lactobacillus* strain is selected from *Lactobacillus paracasei* GMNL-143, *Lactobacillus helveticus* GMNL-164 or *Lactobacillus rhamnosus* GMNL-464. The *L. paracasei* GMNL-143 is deposited at CGMCCCCTCC-China Center for TypeGeneral Microbiological Culture Collection with deposit number CCTCC No. M2014301. The *L. helveticus* GMNL-164 is deposited at CGMCCCCTCC-China Center for TypeGeneral Microbiological Culture Collection with deposit number CCTCC No. M2015609. The *L. rhamnosus* GMNL-464 is deposited at CGMCCCCTCC-China Center for TypeGeneral Microbiological Culture Collection with deposit number CCTCC No. M2015610. The *Lactobacillus* strain is heat-inactivated at 90-121° C. for 15-30 minutes.

The *Lactobacillus* strain is orally administered to the subject in need thereof at dosage of $3\times10^8$-$1\times10^{10}$ cells/time.

A second embodiment of the invention discloses a composition for inhibiting bacterial adhesion of oral pathogens. The composition includes a heat-inactivated *Lactobacillus* strain and a medical acceptable excipient. The heat-inactivated *Lactobacillus* strain is selected from a group consisting of *Lactobacillus paracasei* GMNL-143, *Lactobacillus helveticus* GMNL-164 and *Lactobacillus rhamnosus* GMNL-464. The *L. paracasei* GMNL-143 is deposited at CCTCC-China Center for Type Culture Collection with deposit number CCTCC No. M2014301. The *L. helveticus* GMNL-164 is deposited at CCTCC-China Center for Type Culture Collection with deposit number CCTCC No. M2015609, wherein the *L. rhamnosus* GMNL-464 is deposited at CCTCC-China Center for Type Culture Collection with deposit number CCTCC No. M2015610. The *Lactobacillus* strain is heat-inactivated at 90-121° C. for 15-30 minutes.

The composition includes the *L. paracasei* GMNL-143, the *L. helveticus* GMNL-164 and the *L. rhamnosus* GMNL-464 in the ratio 1:1:1.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE INVENTION

A *Lactobacillus* strain according to the present invention is selected from a group consisting of a *Lactobacillus paracasei* GMNL-143, a *Lactobacillus helveticus* GMNL-164 and a *Lactobacillus rhamnosus* GMNL-464.

In detail, the *L. paracasei* GMNL-143 is isolated from human intestine with morphology after culture at 37° C. for 48 hours includes: circular, retractile, entire edge, 1.0 mm×1.0 mm, milky-white color, smooth surface and convex elevation. Gram-staining shows the *L. paracasei* GMNL-143 is a gram-positive strain. The *L. paracasei* GMNL-143 is a rod type bacilli, which cannot form spore and has no motility. The physiological properties of the *L. paracasei* GMNL-143 includes: growth temperature is 25-45° C., growth pH is pH 4.0-10.0 and belongs to facultative anaerobic bacteria.

Moreover, the *L. paracasei* GMNL-143 has a partial 16S rDNA sequence set forth as SEQ ID NO: 1 and is identified to *L. paracasei* compared to NCBI database. The sugar availability of the *L. paracasei* GMNL-143 is shown in TABLE 1.

TABLE 1

| carbohydrates substrate | result | carbohydrates substrate | result |
|---|---|---|---|
| control | − | esculin ferric citrate | + |
| glycerol | − | salicin | + |
| erythritol | − | D-cellobiose | + |
| D-arabinose | − | D-maltose | + |
| L-arabinose | − | D-lactose | + |
| D-ribose | + | D-melibiose | − |
| D-xylose | − | D-sucrose | + |
| L-xylose | − | D-trehalose | + |
| D-adonitol | + | inulin | − |
| methyl-β-D-xylopyranoside | − | D-melezitose | + |
| D-lactosegalactose | + | D-raffinose | − |
| D-glucose | + | starch | − |
| D-fructose | + | glycogen | − |
| D-mannose | + | xylitol | − |
| L-sorbose | + | gentiobiose | + |
| L-rhamnose | − | D-turanose | + |
| lactosedulcitol | − | D-lyxose | + |
| inositol | + | D-tagatose | + |
| D-mannitol | + | D-fucose | − |
| D-sorbitol | + | L-fucose | − |
| methyl-α-D-mannopyranoside | − | D-arabitol | − |
| methyl-α-D-glucopyranoside | − | L-arabitol | − |
| N-acetyl glucosamine | + | potassium gluconate | + |
| amygdalin | + | potassium 2-ketogluconate | − |
| arbutin | + | potassium 5-ketogluconate | − |

The *L. helveticus* GMNL-164 is isolated from human intestine with morphology after culture at 37° C. for 48 hours includes: circular, undulated edge, 1.2 mm×1.2 mm, gray-white color, dull surface and flat elevation. Gram-staining shows the *L. helveticus* GMNL-164 is a gram-positive strain. The *L. helveticus* GMNL-164 is a rod type bacilli, which cannot form spore and has nomotility. The physiological properties of the *L. helveticus* GMNL-164 includes: growth temperature is 25-45° C., growth pH is pH 4.0-10.0 and belongs to facultative anaerobic bacteria.

Moreover, the *L. helveticus* GMNL-164 has a partial 16S rDNA sequence set forth as SEQ ID NO: 2 and is identified to *L. helveticus* compared to NCBI database. The sugar availability of the *L. helveticus* GMNL-164 is shown in TABLE 2.

TABLE 2

| carbohydrates substrate | result | carbohydrates substrate | result |
|---|---|---|---|
| control | − | esculin ferric citrate | − |
| glycerol | − | salicin | − |
| erythritol | − | D-cellobiose | − |
| D-arabinose | − | D-maltose | − |
| L-arabinose | − | D-lactose | + |
| D-ribose | − | D-melibiose | − |
| D-xylose | − | D-sucrose | − |
| L-xylose | − | D-trehalose | − |
| D-adonitol | − | inulin | − |
| methyl-β-D-xylopyranoside | − | D-melezitose | − |
| D-lactosegalactose | − | D-raffinose | − |
| D-glucose | + | starch | − |
| D-fructose | + | glycogen | − |
| D-mannose | + | xylitol | − |
| L-sorbose | − | gentiobiose | − |
| L-rhamnose | − | D-turanose | − |
| lactosedulcitol | − | D-lyxose | − |

TABLE 2-continued

| carbohydrates substrate | result | carbohydrates substrate | result |
|---|---|---|---|
| inositol | − | D-tagatose | − |
| D-mannitol | − | D-fucose | − |
| D-sorbitol | − | L-fucose | − |
| methyl-α-D-mannopyranoside | − | D-arabitol | − |
| methyl-α-D-glucopyranoside | − | L-arabitol | − |
| N-acetyl glucosamine | + | potassium gluconate | − |
| amygdalin | − | potassium 2-ketogluconate | − |
| arbutin | − | potassium 5-ketogluconate | − |

The *L. rhamnosus* GMNL-464 is isolated from human intestine with morphology after culture at 37° C. for 48 hours includes: circular, glistening, entire edge. 1.5 mm×1.5 mm, milky-white color, smooth surface and convex elevation. Gram-staining shows the *L. rhamnosus* GMNL-464 is a gram-positive strain. The *L. rhamnosus* GMNL-464 is a rod type bacilli, which cannot form spore and has no motility. The physiological properties of the *L. rhamnosus* GMNL-464 includes: growth temperature is 25-45° C., growth pH is pH 4.0-10.0 and belongs to facultative anaerobic bacteria.

Moreover, the *L. rhamnosus* GMNL-464 has a partial 16S rDNA sequence set forth as SEQ ID NO: 3 and is identified to *L. rhamnosus* compared to NCBI database. The sugar availability of the *L. rhamnosus* GMNL-464 is shown in TABLE 3.

TABLE 3

| carbohydrates substrate | result | carbohydrates substrate | result |
|---|---|---|---|
| control | − | esculin ferric citrate | + |
| glycerol | + | salicin | + |
| erythritol | − | D-cellobiose | + |
| D-arabinose | − | D-maltose | + |
| L-arabinose | + | D-lactose | + |
| D-ribose | + | D-melibiose | − |
| D-xylose | − | D-sucrose | + |
| L-xylose | − | D-trehalose | + |
| D-adonitol | − | inulin | − |
| methyl-β-D-xylopyranoside | − | D-melezitose | + |
| D-lactosegalactose | + | D-raffinose | − |
| D-glucose | + | starch | + |
| D-fructose | + | glycogen | − |
| D-mannose | + | xylitol | − |
| L-sorbose | − | gentiobiose | + |
| L-rhamnose | + | D-turanose | + |
| lactosedulcitol | + | D-lyxose | − |
| inositol | − | D-tagatose | − |
| D-mannitol | + | D-fucose | − |
| D-sorbitol | + | L-fucose | − |
| methyl-α-D-mannopyranoside | − | D-arabitol | − |
| methyl-α-D-glucopyranoside | + | L-arabitol | − |
| N-acetyl glucosamine | + | potassium gluconate | + |
| amygdalin | + | potassium 2-ketogluconate | − |
| arbutin | + | potassium 5-ketogluconate | − |

The *L. paracasei* GMNL-143 is deposited at CCTCC-China Center for Type Culture Collection with deposit number CCTCC No. M2014301. The *L. helveticus* GMNL-164 is deposited at CCTCC-China Center for Type Culture Collection with deposit number CCTCC No. M2015609. The *L. rhamnosus* GMNL-464 is deposited at CCTCC-China Center for Type Culture Collection with deposit number CCTCC No. M2015610.

Moreover, the *Lactobacillus* strain can be heat-inactivated, followed by applying to inhibit adhesion of oral pathogens. In this embodiment, for example, the *Lactobacillus* strain is heat-inactivated at 90-121° C. for 15-30 minutes.

Moreover, the *Lactobacillus* strain can be mixed with a medical acceptable excipient to form a composition of inhibiting adhesion of oral pathogens. Alternatively, the *L. paracasei* GMNL-143, the *L. helveticus* GMNL-164 and the *L. rhamnosus* GMNL-464 can be first mixed to form *Lactobacillus* mixture having *L. paracasei* GMNL-143, the *L. helveticus* GMNL-164 and the *L. rhamnosus* GMNL-464 in the ratio 1:1:1, followed by forming the composition of inhibiting adhesion of oral pathogens. It is worthy to note that the *Lactobacillus* strain can also be added into a matrix such as mouthwash, toothpaste, troche, chewing gum and tooth powder to increase the ability of inhibiting adhesion of oral pathogens of the matrix thereof. Specifically, the matrix including the *Lactobacillus* strain can be applied in a dosage and time listed in TABLE 4, which is appreciated by a person having ordinary skill in the art.

TABLE 4

| matrix | dosage | time |
|---|---|---|
| mouthwash | $1 \times 10^9$ cells/time | 30 seconds |
| toothpaste | $7 \times 10^8$-$1 \times 10^9$ cells/time | 1 minute |
| troche | $3 \times 10^8$ cells/time | 10-20 minutes |
| chewing gum | $2 \times 10^9$ cells/time | 10-30 minutes |
| tooth powder | $1 \times 10^{10}$ cells/time | 1 minute |

To evaluate the *Lactobacillus* strain can inhibit the adhesion of oral pathogens, the *Lactobacillus* strain is heat-inactivated at 90-121° C. for 15-30 minutes, followed by cooling to room temperature to carry out the following trials.

Trial (A): *L. paracasei* GMNL-143 inhibits adhesion of *S. mutans* (ATCC 25175)

Referring to TABLE 5, *S. mutans* (ATCC 25175) is used in trail (A). *L. paracasei* GMNL-143 (0.5 mL) and *S. mutans* (ATCC 25175, 0.5 mL) is mixed and stood for 5 minutes. The upper solution (500 μL) is added into a 24-well plate with sterile slides and incubated at 37° C. for 2 hours. The upper solution is then removed and methanol is added after the slide is washed by phosphate buffer saline (PBS). Finally, the slide is stained by Giemsa stain to evaluate the number of *S. mutans* adhering on the slide.

TABLE 5

| groups | condition |
|---|---|
| A0 | PBS + *S. mutans* (ATCC 25175) |
| A1 | *L. paracasei* GMNL-33 + *S. mutans* (ATCC 25175) |
| A2 | *L. paracasei* GMNL-143 + *S. mutans* (ATCC 25175) |

Figure 1A:
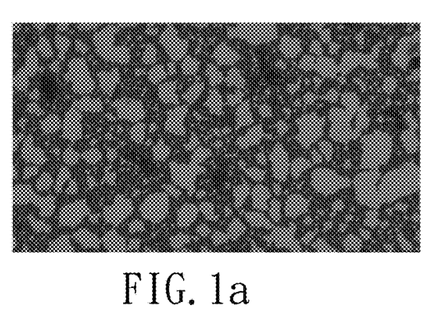
FIG. 1a depicts a Giemsa stain showing the adhesion of *S. mutans* on the slide after treating by PBS in trial (A).
Figure 1B:
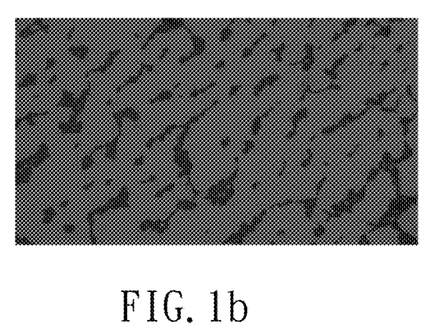
FIG. 1b depicts a Giemsa stain showing the adhesion of *S. mutans* on the slide after treating by *L. paracasei* GMNL-33 in trial (A).
Figure 1C:
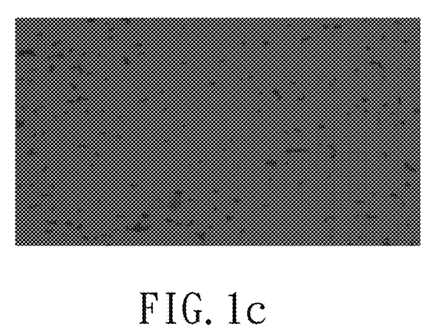
FIG. 1c depicts a Giemsa stain showing the adhesion of *S. mutans* on the slide after treating by *L. paracasei* GMNL-143 in trial (A).

With reference to FIG. 1a, *S. mutans* (ATCC 25175) adheres on the slides in the presence of PBS (group A0). In contrast, as shown in FIGS. 1b and 1c, treatment of *L. paracasei* GMNL-33 and GMNL-143 can reduce the adhesion of *S. mutans* (ATCC 25175) on the slides with the *L. paracasei* GMNL-143 according to the present invention showing a better effect.

Trial (B): *L. paracasei* GMNL-143 inhibits adhesion of *S. mutans* (BCRC 16002)

Figure 2A:
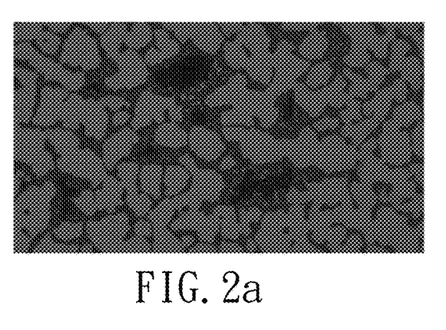
FIG. 2a depicts a Giemsa stain showing the adhesion of *S. mutans* on the slide after treating by PBS in trial (B).
Figure 2B:
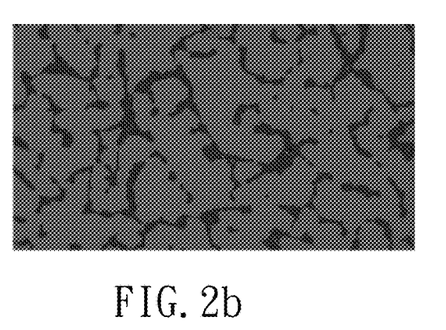
FIG. 2b depicts a Giemsa stain showing the adhesion of *S. mutans* on the slide after treating by *L. paracasei* GMNL-33 in trial (B).
Figure 2C:
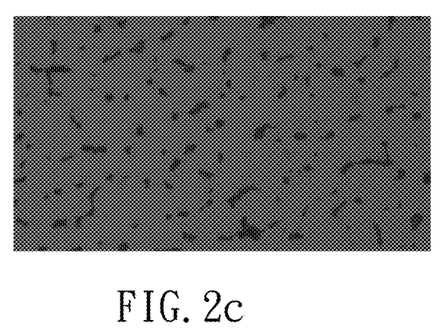
FIG. 2c depicts a Giemsa stain showing the adhesion of *S. mutans* on the slide after treating by *L. paracasei* GMNL-143 in trial (B).

Referring to TABLE 6, *S. mutans* (BCRC 16002) is used in trial (B). With respect to FIGS. 2a-2c, similar to the results mentioned above, treatment of *L. paracasei* GMNL-33 and GMNL-143 can reduce the adhesion of *S. mutans* (BCRC 16002) on the slides with the *L. paracasei* GMNL-143 according to the present invention showing a better effect.

TABLE 6

| groups | condition |
|---|---|
| B0 | PBS + S. mutans (BCRC 16002) |
| B1 | L. paracasei GMNL-33 + S. mutans (BCRC 16002) |
| B2 | L. paracasei GMNL-143 + S. mutans (BCRC 16002) |

Trial (C): L. helveticus GMNL-164 inhibits adhesion of P. gingivalis (ATCC 33277)

Smulow-Clickman gingival cells (SG cells) are used in trial (C). Referring to TABLE 7, same amount of L. helveticus GMNL-164 and P. gingivalis (ATCC 33277) are mixed. The upper solution (100 μL) is added into a 24-well plate coated SG cells (3×10$^5$ cells/well) and incubated at 37° C. for 2 hours. The upper solution is then removed. The SG cells in each well are collected and bacterial DNA adhering on the SG cells is extracted. Real-time PCR using primer pairs set forth as SEQ ID NOS: 4 and 5 is finally carried out and $2^{-\Delta CT}$ is calculated (as shown in FIG. 3).

TABLE 7

| groups | condition |
|---|---|
| C0 | PBS + P. gingivalis (ATCC 33277) |
| C1 | L. paracasei GMNL-33 + P. gingivalis (ATCC 33277) |
| C2 | L. helveticus GMNL-164 + P. gingivalis (ATCC 33277) |

Figure 3:
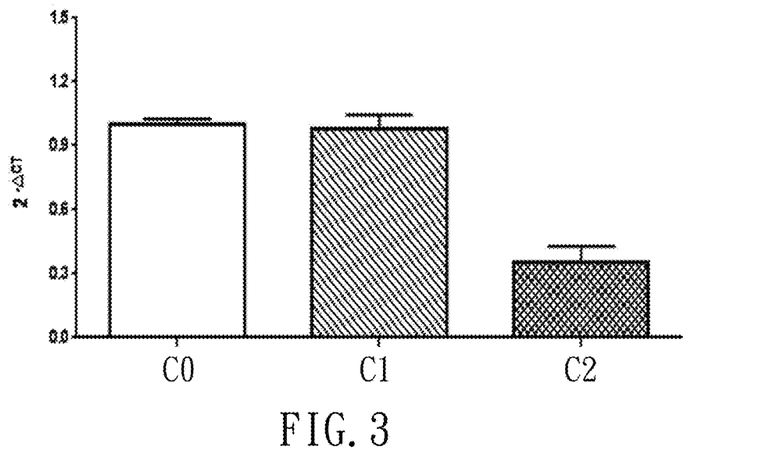
FIG. 3 depicts a bar chart showing the adhesion of *P. gingivalis* on SG cells after treating by PBS (group C0), *L. paracasei* GMNL-33 (group C1) and *L. helveticus* GMNL-164 (group C2) in trial (C).

Referring to FIG. 3, both L. paracasei GMNL-33 and L. helveticus GMNL-164 inhibit P. gingivalis adhering on SG cells, with L. helveticus GMNL-164 according to the invention shows a better effect.

Trial (D): L. helveticus GMNL-164 inhibits adhesion of P. intermedia (ATCC 25611)

The SG cells are also used in trial (D). Referring to TABLE 8, same amount of L. helveticus GMNL-164 and P. intermedia (ATCC 25611) are mixed. The upper solution (100 μL) is added into a 24-well plate coated SG cells (3×10$^5$ cells/well) and incubated at 37° C. for 2 hours. The upper solution is then removed. The SG cells in each well are collected and bacterial DNA adhering on the SG cells is extracted. Real-time PCR using primer pairs set forth as SEQ ID NOS: 6 and 7 is finally carried out and $2^{-\Delta CT}$ is calculated (as shown in FIG. 4).

TABLE 8

| groups | condition |
|---|---|
| D0 | PBS + P. intermedia (ATCC 25611) |
| D1 | L. paracasei GMNL-33 + P. intermedia (ATCC 25611) |
| D2 | L. helveticus GMNL-164 + P. intermedia (ATCC 25611) |

Figure 4:
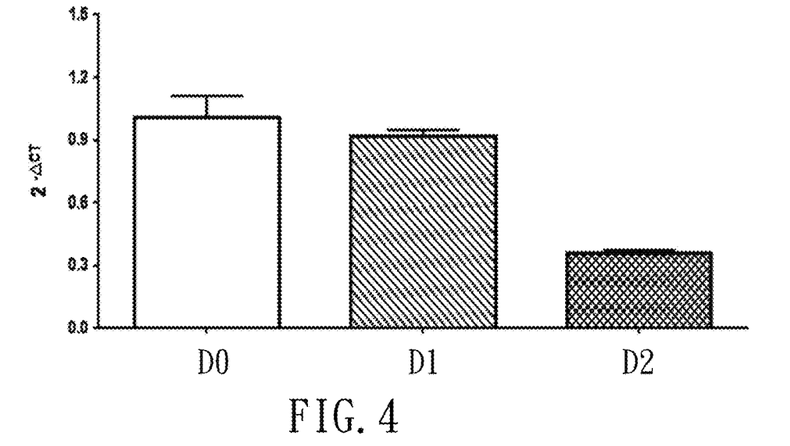
FIG. 4 depicts a bar chart showing the adhesion of *P. intermedia* on SG cells after treating by PBS (group D0), *L. paracasei* GMNL-33 (group D1) and *L. helveticus* GMNL-164 (group D2) in trial (D).

Referring to FIG. 4, both L. paracasei GMNL-33 and L. helveticus GMNL-164 inhibit P. intermedia adhering on SG cells, with L. helveticus GMNL-164 according to the invention shows a better effect.

Trial (E): L. rhamnosus GMNL-464 inhibits adhesion of Fusobacterium nucleatum (ATCC 25586)

The SG cells are also used in trial (E). Referring to TABLE 9, same amount of L. rhamnosus GMNL-464 and F. nucleatum (ATCC 25586) are mixed. The upper solution (100 μL) is added into a 24-well plate coated SG cells (3×10$^5$ cells/well) and incubated at 37° C. for 2 hours. The upper solution is then removed. The SG cells in each well are collected and bacterial DNA adhering on the SG cells is extracted. Real-time PCR using primer pairs set forth as SEQ ID NOS: 8 and 9 is finally carried out and $2^{-\Delta CT}$ is calculated (as shown in FIG. 5).

TABLE 9

| groups | condition |
|---|---|
| E0 | PBS + F. nucleatum (ATCC 25586) |
| E1 | L. paracasei GMNL-33 + F. nucleatum (ATCC 25586) |
| E2 | L. rhamnosus GMNL-464 + F. nucleatum (ATCC 25586) |

Figure 5:
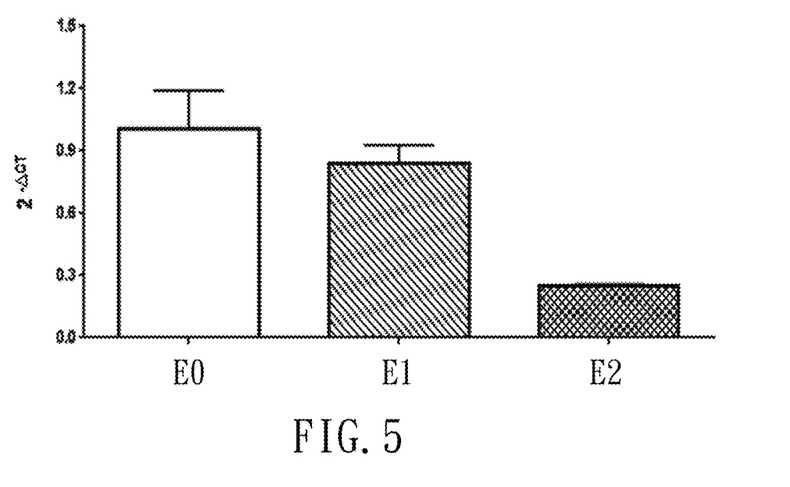
FIG. 5 depicts a bar chart showing the adhesion of *F. nucleatum* on SG cells after treating by PBS (group E0), *L. paracasei* GMNL-33 (group E1) and *L. rhamnosus* GMNL-464 (group E2) in trial (E).

Referring to FIG. 5, both L. paracasei GMNL-33 and L. rhamnosus GMNL-464 inhibit F. nucleatum adhering on SG cells, with L. rhamnosus GMNL-464 according to the invention shows a better effect.

Trial (F): Synergetic effects of L. paracasei GMNL-143, L. helveticus GMNL-164 and L. rhamnosus GMNL-464

In trial (F), same amount of L. paracasei GMNL-143, L. helveticus GMNL-164 and L. rhamnosus GMNL-464 is mixed to form the Lactobacillus mixture. Sterile water is used to further form a mouthwash with a low-dose Lactobacillus mixture (5×10$^7$ cells/mL, group F1), with a middle-dose Lactobacillus mixture (5×10$^8$ cells/mL, group F2) and with a high-dose Lactobacillus mixture (5×10$^9$ cells/mL, group F3). The sterile water without the Lactobacillus mixture is used as the control (group F0).

In detail, sterile cotton swabs are used to collect oral bacteria before gargling with the mouthwash (T0), 1 hour after gargling with the mouthwash (T1) and 2.5 hours gargling with the mouthwash (T2), respectively. The cotton swab with oral bacteria is put into sterile water (0.5 mL), vortexed for 3-5 seconds, stood for 1 hour at room temperature, and centrifugated at 13,000 rpm for 10 minutes. The cotton swab is then removed and the sterile water with oral bacteria is then centrifugated at 13,000 rpm for 10 minutes. After discarding the supernatant, DNA of the pellet is extracted. Finally, real-time PCR is carried out using the primers with DNA sequence set forth as SEQ ID NOS: 10 and 11, the primers with DNA sequence set forth as SEQ ID NOS: 3 and 4, or the primers with DNA sequence set forth as SEQ ID NOS: 8 and 9 to quantify S. mutans, P. gingivalis or F. nucleatum in oral microbiota, respectively. Moreover, the primers with DNA sequence set forth as SEQ ID NOS: 12 and 13 are used to quantify the total oral bacteria.

Figure 6A:
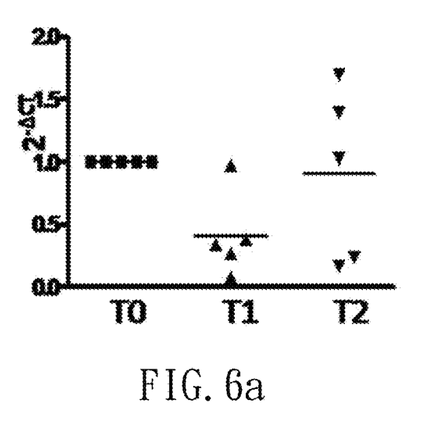
FIG. 6a depicts a point chart showing the relative level of oral *S. mutans* before and after gargling with control mouthwash (group F0) in trial (F).
Figure 6B:
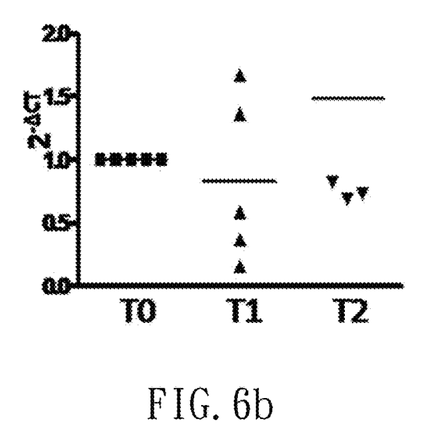
FIG. 6b depicts a point chart showing the relative level of oral *P. gingivalis* before and after gargling with control mouthwash (group F0) in trial (F).
Figure 6C:
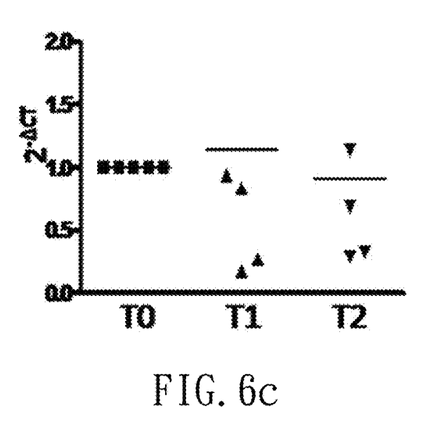
FIG. 6c depicts a point chart showing the relative level of oral *F. nucleatum* before and after gargling with control mouthwash (group F0) in trial (F).
Figure 6D:
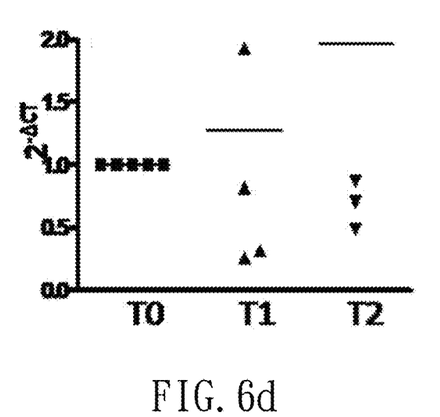
FIG. 6d depicts a point chart showing the relative level of total oral bacteria before and after gargling with control mouthwash (group F0) in trial (F).
Figure 7A:
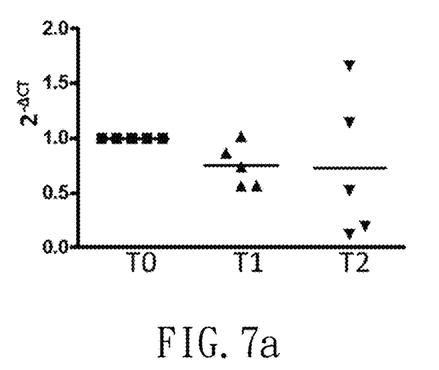
FIG. 7a depicts a point chart showing the relative level of oral *S. mutans* before and after gargling with the low-dose mouthwash (group F1) in trial (F).
Figure 7B:
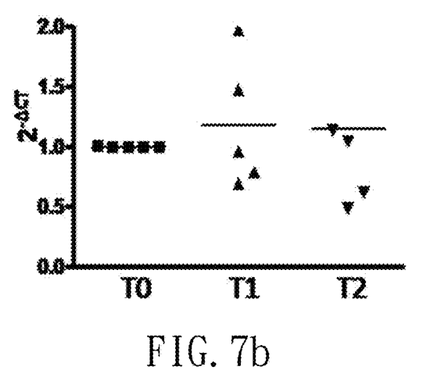
FIG. 7b depicts a point chart showing the relative level of oral *P. gingivalis* before and after gargling with the low-dose mouthwash (group F1) in trial (F).
Figure 7C:
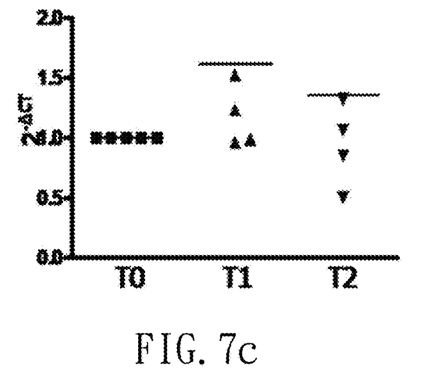
FIG. 7c depicts a point chart showing the relative level of oral *F. nucleatum* before and after gargling with the low-dose mouthwash (group F1) in trial (F).
Figure 7D:
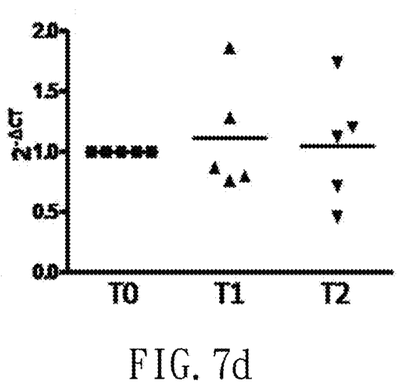
FIG. 7d depicts a point chart showing the relative level of total oral bacteria before and after gargling with the low-dose mouthwash (group F1) in trial (F).
Figure 8A:
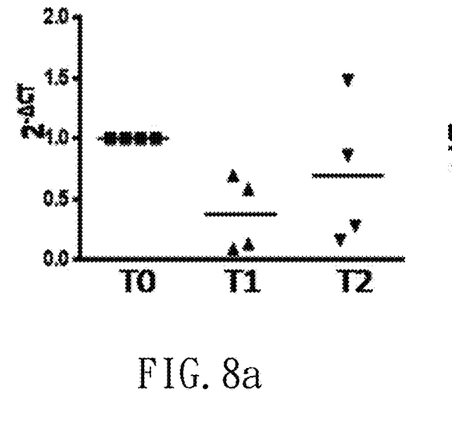
FIG. 8a depicts a point chart showing the relative level of oral *S. mutans* before and after gargling with the middle-dose mouthwash (group F2) in trial (F).
Figure 8B:
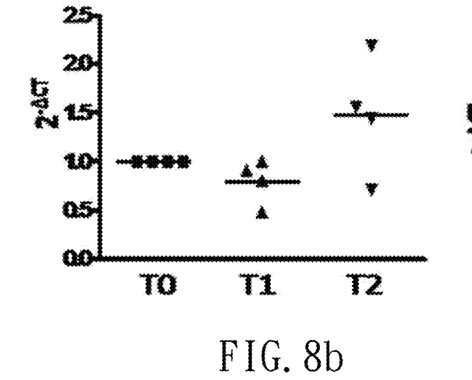
FIG. 8b depicts a point chart showing the relative level of oral *P. gingivalis* before and after gargling with the middle-dose mouthwash (group F2) in trial (F).
Figure 8C:
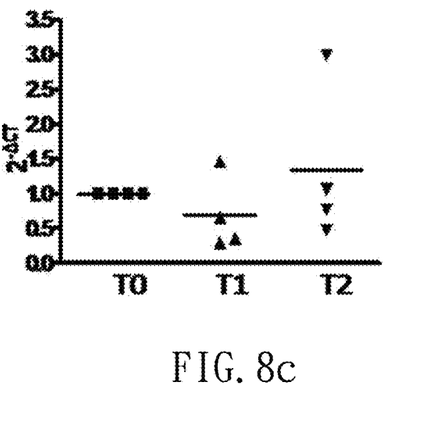
FIG. 8c depicts a point chart showing the relative level of oral *F. nucleatum* before and after gargling with the middle-dose mouthwash (group F2) in trial (F).
Figure 8D:
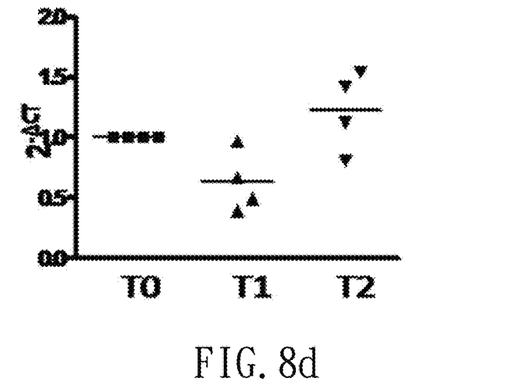
FIG. 8d depicts a point chart showing the relative level of total oral bacteria before and after gargling with the middle-dose mouthwash (group F2) in trial (F).
Figure 9A:
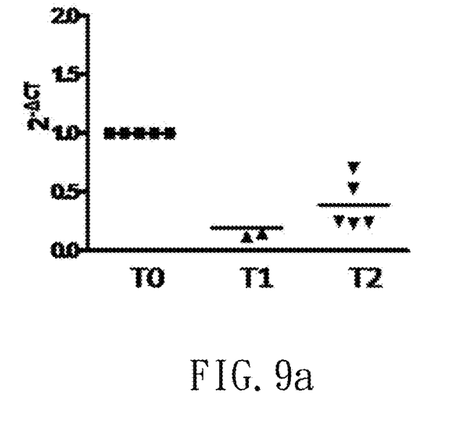
FIG. 9a depicts a point chart showing the relative level of oral *S. mutans* before and after gargling with the high-dose mouthwash (group F3) in trial (F).
Figure 9B:
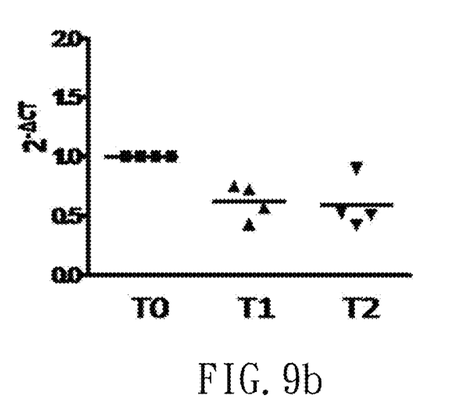
FIG. 9b depicts a point chart showing the relative level of oral *P. gingivalis* before and after gargling with the high-dose mouthwash (group F3) in trial (F).
Figure 9C:
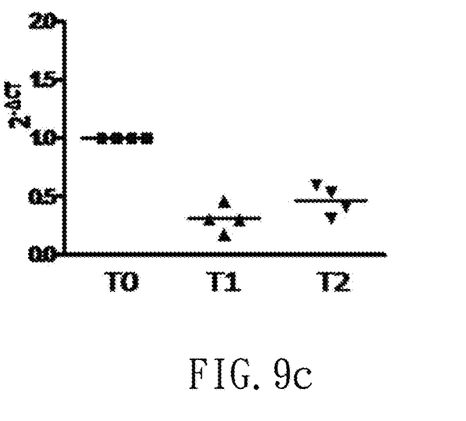
FIG. 9c depicts a point chart showing the relative level of oral *F. nucleatum* before and after gargling with the high-dose mouthwash (group F3) in trial (F).
Figure 9D:
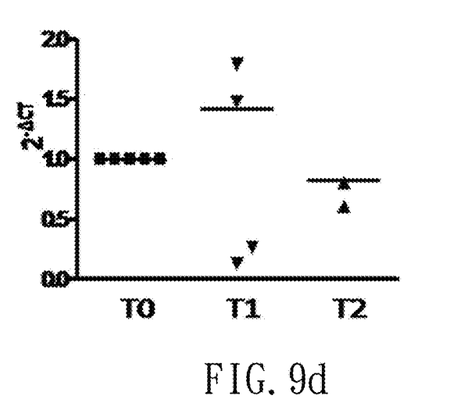
FIG. 9d depicts a point chart showing the relative level of total oral bacteria before and after gargling with the high-dose mouthwash (group F3) in trial (F).

FIGS. 6a-6c show relative amounts of S. mutans, P. gingivalis and F. nucleatum before and after gargling with the control mouthwash (group F0), respectively. FIG. 6d shows the total oral bacteria before and after gargling with the control mouthwash (group F0), respectively. Moreover, FIGS. 7a-7d, 8a-8d and 9a-9d show the results before and after gargling with the low-dose, middle-dose and high-dose mouthwash (groups F1, F2 and F3), respectively. That is, the dose of the Lactobacillus mixture is positive correlated to the decrease of S. mutans, P. gingivalis and F. nucleatum. Furthermore, the mouthwash of group F3 shows a significant bacteriostatic effect.

In view of the foregoing, the heat-inactivated Lactobacillus strain according to the present invention can prevent oral pathogens from adhesion on oral cavity, adjusting distribution of the oral microbiota. Therefore, the Lactobacillus strain can be used to improve oral health.

Moreover, the composition for inhibiting bacterial adhesion of oral pathogens according to the present invention includes the L. paracasei GMNL-143, the L. helveticus GMNL-164 and the L. rhamnosus GMNL-464. The L. paracasei GMNL-143, the L. helveticus GMNL-164 and the L. rhamnosus GMNL-464 show synergetic effect on preventing oral pathogens from adhering on oral cavity. Therefore, the composition for inhibiting bacterial adhesion of oral pathogens according to the present invention shows a better effect on adjusting the distribution of oral microbiota, improving oral health.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for inhibiting bacterial adhesion of *Streptococcus mutans*, comprising administering a heat-inactivated *Lactobacillus paracasei* GMNL-143 to a subject in need to inhibit bacterial adhesion of *S. mutans*, wherein the *L. paracasei* GMNL-143 is deposited at CCTCC-China Center for Type Culture Collection with deposit number CCTCC No. M2014301, wherein the *L. paracasei* GMNL-143 is heat-inactivated at 90-121° C. for 15-30 minutes.

2. The method for inhibiting bacterial adhesion of *S. mutans* according to claim 1, wherein the *Lactobacillus paracasei* GMNL-143 is orally administered to the subject in need at dosage of $3\times10^8$-$1\times10^{10}$ cells/time.

* * * * *

```
                         SEQUENCE LISTING

<160> NUMBER OF SEQ ID NOS: 13

<210> SEQ ID NO 1
<211> LENGTH: 525
<212> TYPE: DNA
<213> ORGANISM: Lactobacillus paracasei

<400> SEQUENCE: 1
ctaagtgtgc tatacatgca agtcgaacga gttctcgttg atgatcggtg cttgcaccga      60
gattcaacat ggaacgagtg acggacgggt gagtaacacg tgggtaacct gcccttaagt    120
gggggataac atttggaaac agatgctaat accgcataga tccaagaacc gcatggttct    180
tggctgaaag atggcgtaag ctatcgcttt tggatggacc cgcggcgtat tagctagttg    240
gtgaggtaat ggctcaccaa ggcgatgata cgtagccgaa ctgagaggtt gatcggccac    300
attgggactg agacacggcc caaactccta cgggaggcag cagtagggaa tcttccacaa    360
tggacgcaag tctgatggag caacgccgcg tgagtgaaga aggctttcgg gtcgtaaaac    420
tctgttgttg gagaagaatg gtcggcagag taactgttgt cggcgtgacg gtatccaacc    480
agaaagccac ggctaactac gtgccagcag ccgcggtaat actaa                    525

<210> SEQ ID NO 2
<211> LENGTH: 520
<212> TYPE: DNA
<213> ORGANISM: Lactobacillus helveticus

<400> SEQUENCE: 2
cacgtgtcta atactggaag tcgagcgagc ataaccagca gatttacttc ggtaatgacg      60
ctggggacgc gagcggcgga tgggtgagta acacgtgggg aacctgcccc atagcctggg    120
ataccacttg gaaacaggtg ctaataccgg ataagaaagc agatcgcatg atcagcttat    180
aaaaggcggc gtaagctgtc gctatgggat ggccccgcgg ggcattagct agttggtaag    240
ggaacggctt accaaggcaa tgatgcatag ccgatttgag agactgatcg ccacattgg     300 gactgagaca cggcccaaac tcatacggga ggcagcagta gggaatcttc cacaatggac    360
gcaagtctga tggagcaacg ccgcgtgagt gaagaaggtt ttcggatcgt aaagctctgt    420
tgttggtgaa gaaggataga ggtagtaact ggcctttatt tgacggtaat caaccagaaa    480
gtcacggcta actacgtgcc agcagccggg ggtaatacaa                          520

<210> SEQ ID NO 3
<211> LENGTH: 528
<212> TYPE: DNA
<213> ORGANISM: Lactobacillus rhamnosus

<400> SEQUENCE: 3
gcaaatgcgc gtgctataca tgcagtcgaa cgagttctga ttattgaaag gtgcttgcat      60
cttgatttaa ttttgaacga gtggcggacg ggtgagtaac acgtgggtaa cctgccctta    120
agtgggggat aacatttgga aacagatgct aataccgcat aaatccaaga accgcatggt    180
tcttggctga agatggcgt aagctatcgc ttttggatgg acccgcggcg tattagctag    240
ttggtgaggt aacggctcac caaggcaatg atacgtagcc gaactgagag gttgatcggc    300
cacattggga ctgagacacg gcccaaactc ctacgggagg cagcagtagg gaatcttcca    360
```

```
caatggacgc aagtctgatg gagcaacgcc gcgtgagtga agaaggcttt cgggtcgtaa    420
aactctgttg ttggagaaga atggtcggca gagtaactgt tgtcggcgtg acggtatcca    480
accagaaagc cacggctaac tacgtgccag cagccggggg taatacaa                 528
```

```
<210> SEQ ID NO 4
<211> LENGTH: 20
<212> TYPE: DNA
<213> ORGANISM: Artificial Sequence
<220> FEATURE:
<223> OTHER INFORMATION: primer for quantifying Porphyromonas gingivalis

<400> SEQUENCE: 4
ataggcatgc gtcccattag                                                 20

<210> SEQ ID NO 5
<211> LENGTH: 20
<212> TYPE: DNA
<213> ORGANISM: Artificial Sequence
<220> FEATURE:
<223> OTHER INFORMATION: primer for quantifying Porphyromonas gingivalis

<400> SEQUENCE: 5
cgtaggagtc tggtccgtgt                                                 20

<210> SEQ ID NO 6
<211> LENGTH: 25
<212> TYPE: DNA
<213> ORGANISM: Artificial Sequence
<220> FEATURE:
<223> OTHER INFORMATION: primer for quantifying Prevotella intermedia

<400> SEQUENCE: 6
cgtggaccaa agattcatcg gtgga                                           25

<210> SEQ ID NO 7
<211> LENGTH: 20
<212> TYPE: DNA
<213> ORGANISM: Artificial Sequence
<220> FEATURE:
<223> OTHER INFORMATION: primer for quantifying Prevotella intermedia

<400> SEQUENCE: 7
ccgctttact ccccaacaaa                                                 20

<210> SEQ ID NO 8
<211> LENGTH: 23
<212> TYPE: DNA
<213> ORGANISM: Artificial Sequence
<220> FEATURE:
<223> OTHER INFORMATION: primer for quantifying Fusobacterium nucleatum

<400> SEQUENCE: 8
cgcagaaggt gaaagtcctg tat                                             23

<210> SEQ ID NO 9
<211> LENGTH: 23
<212> TYPE: DNA
<213> ORGANISM: Artificial Sequence
<220> FEATURE:
<223> OTHER INFORMATION: primer for quantifying Fusobacterium nucleatum

<400> SEQUENCE: 9
tggtcctcac tgattcacac aga                                             23
```

```
<210> SEQ ID NO 10
<211> LENGTH: 20
<212> TYPE: DNA
<213> ORGANISM: Artificial Sequence
<220> FEATURE:
<223> OTHER INFORMATION: primer for quantifying Streptococcus mutans

<400> SEQUENCE: 10
cgcgtaggta acctgcctat                                              20

<210> SEQ ID NO 11
<211> LENGTH: 20
<212> TYPE: DNA
<213> ORGANISM: Artificial Sequence
<220> FEATURE:
<223> OTHER INFORMATION: primer for quantifying Streptococcus mutans

<400> SEQUENCE: 11
gctaatacaa cgcaggtcca                                              20

<210> SEQ ID NO 12
<211> LENGTH: 20
<212> TYPE: DNA
<213> ORGANISM: Artificial Sequence
<220> FEATURE:
<223> OTHER INFORMATION: primer for quantifying oral flora

<400> SEQUENCE: 12
gtgstgcayg gytgtcgtca                                              20

<210> SEQ ID NO 13
<211> LENGTH: 20
<212> TYPE: DNA
<213> ORGANISM: Artificial Sequence
<220> FEATURE:
<223> OTHER INFORMATION: primer for quantifying oral flora

<400> SEQUENCE: 13
acgtcrtccm caccttcctc                                              20
```